United States Patent [19]

Bordier

[11] Plant 4,245

[45] May 2, 1978

[54] ERIOBOTRYA HYBRID

[75] Inventor: Ernest P. Bordier, Laguna Hills, Calif.

[73] Assignee: Bordiers Nursery, Inc., Santa Ana, Calif.

[21] Appl. No.: 747,972

[22] Filed: Dec. 6, 1976

[51] Int. Cl.[2] ..... A01H 5/00

[52] U.S. Cl. ..... Plt./54

[58] Field of Search ..... Plt./54

*Primary Examiner*—Robert E. Bagwill
*Attorney, Agent, or Firm*—George F. Bethel; P. K. Bethel

[57] ABSTRACT

A novel Eriobotrya having large panicles of distinctive, light pink blossoms, and leaves which are coppery-red when new, turning to a shiny, dark green.

2 Drawing Figures

BACKGROUND OF THE INVENTION

The present invention relates to a new and distinct variety of Eriobotrya Hybrid plant. More particularly, it relates to a plant of the foregoing genus (family Rosaceae) which is an evergreen shrub.

NOVEL CHARACTERISTICS

My new and distinct variety is characterized as to its novelty by its shiny dark green foliage throughout the year. Its new growth has a coppery-red color and a slight pubescence. It has a robust growing habit and large pyramidal panicle of the flowers. The flowers are a light pink color.

DIFFERENCE FROM ANTECEDENTS

The new variety differs from its seed parent, *Eriobotrya deflexa,* by its large, leathery and shiny leaves; its many branched habit; and by its large, light pink pyramidal flower heads. To the contrary, the flowers of the parent plant are off-white in color. The panicles of flowers of the new variety are described as being large-pyramidal, whereas the parent has broad flat heads. The color of the leaves of the new variety are of a shiny dark green, while the leaf color of the parent is a lighter green and is not as shiny.

AREA LOCATION AND CHARACTER

I discovered this new variety on my cultivated property located at 1303 South Bonnie Cove Ave., in the city of Glendora, County of Los Angeles, State of Calif., in June of 1970. The new variety originated as a chance seedling of cultivated *Eriobotrya deflexa,* which is believed to be unpatented, with the pollen parent being unknown.

ASEXUAL REPRODUCTION

The new variety has been asexually reproduced by me on my cultivated property in Glendora, Calif. and my cultivated property located at 7231 Irvine Boulevard, County of Orange, State of Calif., by cuttings. Over a thousand cuttings of the new and distinct variety have been made since May of 1971. In all instances, the descendants have exhibited the distinguishing characteristics of the new variety, thereby establishing that the strain is true. The plant does not produce seed.

DETAILED DESCRIPTION OF THE EMBODIMENT

A detailed description of my new and distinct variety of Eriobotrya Hybrid follows. The accompanying illustrations in full color, utilizing color photography show the close-up view of the flowers and foliage. To facilitate identification of the important colors, the color terminology scheme of the British Horticultural Colour Charts has been followed. The color of the leaves and flowers in the accompanying illustrations are as close as can be reproduced by color photography.

THE PLANT

Type: Evergreen bush.

Parentage: Chance seedling from *Eriobotrya deflexa,* believed to be unpatented, pollen parent unknown.

Growth habit: The bush has an upright many branched habit.

Size: The bush reaches a height of approximately 8 feet and a width of 6 to 8 feet.

Foliage:

- *Quantity.*—Abundant.
- *Shape.*—The leaves are elliptical with the upper half being serrate.
- *Size.*—The full grown leaves are 6 to 8 inches in length and are 2 to 2½ inches in width.
- *Arrangement.*—The leaves are alternate on the stem.
- *Color.*—Upper side — Ivy Green 0001060. Under side — Spinach Green 0000960.
- *Appearance.*—Shiny.
- *Petiole.*—Average 1½ inches in length. Veins: Depressed on the upper side; lighter than background on the under side. Texture: Coriaceous.

THE FLOWER

Blooming habit: The plant blooms once a year in March and April in Southern California.

Shape of inflorescence: In large pyramidal terminal panicles, wherein each panicle bears approximately 75 to 100 flowers and is approximately 6 to 8 inches long and 4 to 6 inches wide.

Number of petals: Five.

Shape of petals: Obovate.

Peduncle: The flowers are attached to pubescent peduncles that are one-fourth to one-half inch in length.

Color: Dawn Pink 523/3.

Fragrance: Slight.

Sepals: Five, united and pubescent.

Note: These descriptions are based upon mature plants in good soil in Orange County, Calif.

Having described my invention, I claim:

1. A new and distinct variety of *Eriobotrya deflexa,* substantially as shown and described, characterized particularly as to its novelty by:

the distinctive and unique coloring of the flowers which are light pink;

the large pyramidal panicles of the flowers;

by the shiny dark green leaves; and, by the new leaves that are coppery-red.

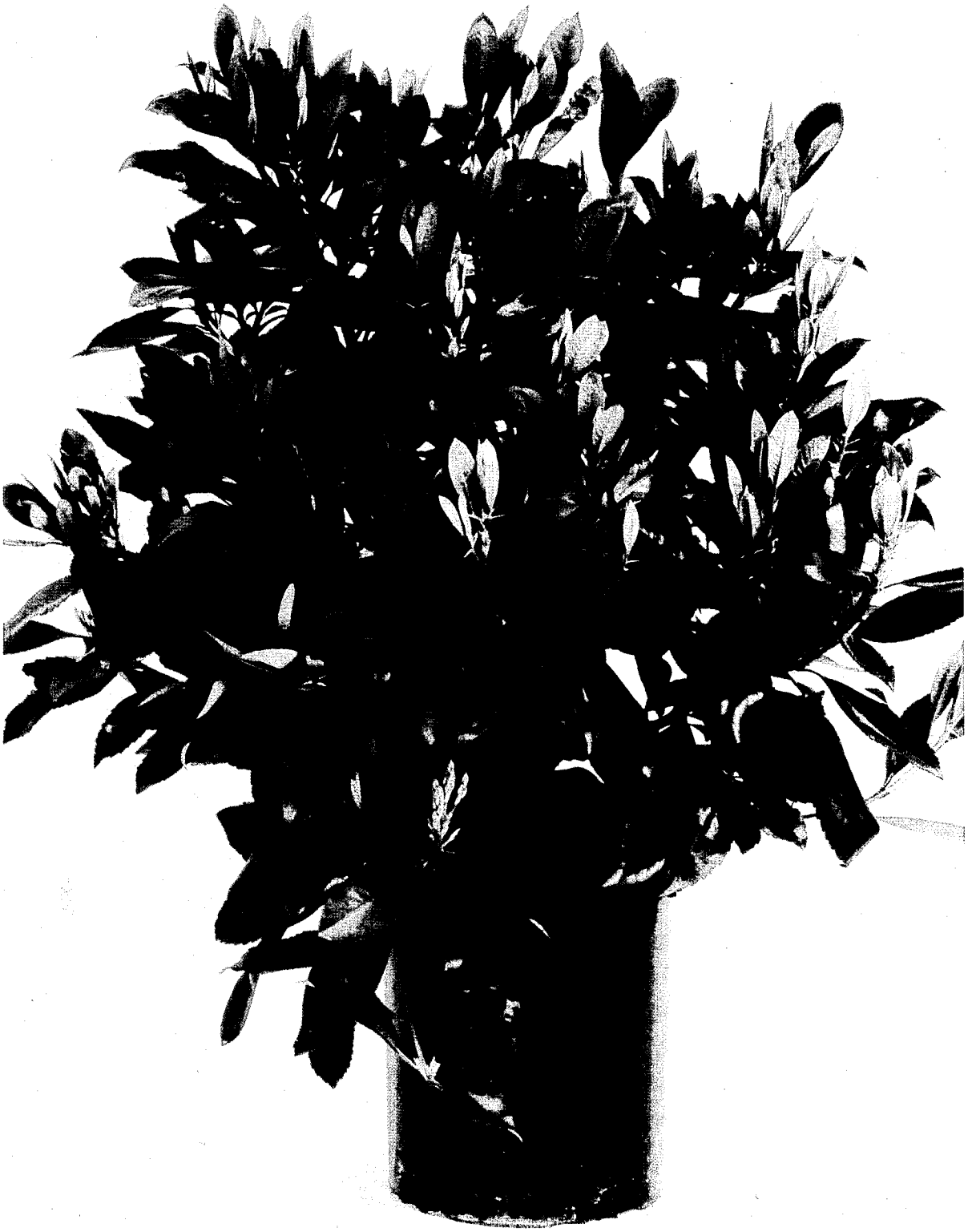

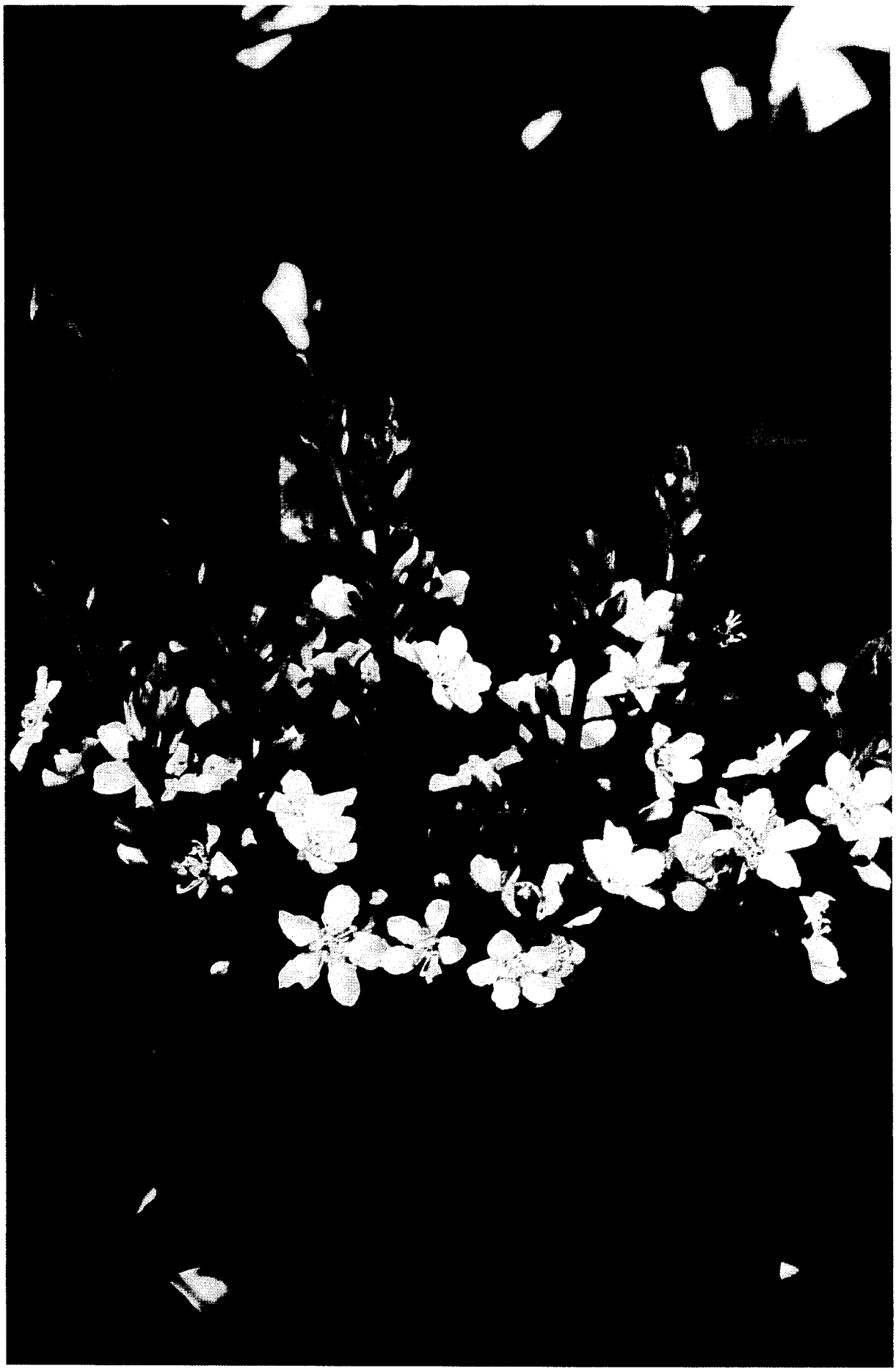

* * * * *